(12) United States Patent
Schiller (10) Patent No.: US 9,844,104 B1
(45) Date of Patent: Dec. 12, 2017

(54) ELECTRODE JOINING APPARATUS (71) Applicant: Contractors & Industrial Supply Company, Inc., Nashville, TN (US)

(72) Inventor: Tom D. Schiller, Franklin, TN (US)

(73) Assignee: Contractors & Industrial Supply Company, Inc., Nashville, TN (US)

( * ) Notice: Subject to any disclaimer, the term of this patent is extended or adjusted under 35 U.S.C. 154(b) by 259 days.

(21) Appl. No.: 14/693,673

(22) Filed: Apr. 22, 2015

Related U.S. Application Data (60) Provisional application No. 61/982,337, filed on Apr. 22, 2014.

(51) Int. Cl.
*H05B 7/14* (2006.01)
*H05B 7/102* (2006.01)
*H05B 7/109* (2006.01)

(52) U.S. Cl.
CPC ............... *H05B 7/14* (2013.01); *H05B 7/102* (2013.01); *H05B 7/109* (2013.01)

(58) Field of Classification Search
CPC ...... B23K 9/133; B23K 9/1336; B23K 9/028; B23K 9/16; B23K 9/164; H05B 7/14; H05B 7/102; H05B 7/109
See application file for complete search history.

(56) References Cited

U.S. PATENT DOCUMENTS

| | | |
|---|---|---|
| 2,226,652 A | 12/1940 | York |
| 2,494,775 A | 1/1950 | Moore |
| 3,249,673 A | 5/1966 | Moore |
| 3,517,954 A | 6/1970 | Snyder et al. |
| 3,600,031 A | 8/1971 | Coleman et al. |
| 3,752,896 A | 8/1973 | Zimmermann et al. |
| 3,781,449 A | 12/1973 | Wolf et al. |
| 3,790,204 A | 2/1974 | Lighthipe, Jr. et al. |
| 3,796,818 A | 3/1974 | Yuasa et al. |

(Continued)

FOREIGN PATENT DOCUMENTS

| | | |
|---|---|---|
| IT | 1052996 B | 8/1981 |
| IT | 1192885 B | 5/1988 |

(Continued)

OTHER PUBLICATIONS

U.S. Appl. No. 14/693,652, filed Apr. 22, 2015, Schiller.

(Continued)

*Primary Examiner* — Carl Arbes
(74) *Attorney, Agent, or Firm* — Waller Lansden Dortch & Davis, LLP; Matthew C. Cox (57) ABSTRACT

An electrode joining apparatus for joining a free electrode to a fixed electrode, the fixed electrode having a top end. The apparatus can include an electrode holder configured to selectively hold the fixed electrode. A torque device can be positioned above the electrode holder, the torque device configured to grip and spin the free electrode to join the free electrode to the fixed electrode. A blowout jet can be oriented to selectively force a stream of gas toward the top end of the fixed electrode when the fixed electrode is held by the electrode holder. As such, the blowout jet can help remove dust, debris, or graphite residue on the top end of the fixed electrode before joining of the free electrode to the fixed electrode. The fixed electrode can include a threaded socket, the blow jet oriented to force the stream of gas toward the threaded socket.

8 Claims, 8 Drawing Sheets

(56) References Cited

U.S. PATENT DOCUMENTS

| | | | |
|---|---|---|---|
| 3,814,828 A | 6/1974 | Gazda | |
| 4,154,974 A | 5/1979 | Wynne | |
| 4,162,368 A | 7/1979 | Brazier | |
| 4,167,643 A * | 9/1979 | Charnock | H05B 7/14 373/91 |
| 4,185,158 A | 1/1980 | Koga et al. | |
| 4,317,951 A | 3/1982 | Boudeau et al. | |
| 4,323,717 A | 4/1982 | Garner et al. | |
| 4,400,815 A | 8/1983 | Dunn et al. | |
| 4,420,838 A | 12/1983 | Dunn et al. | |
| 4,665,530 A | 5/1987 | Corbethau | |
| 4,703,492 A | 10/1987 | Sekiguchi et al. | |
| 4,736,384 A * | 4/1988 | Sakai | H05B 7/14 373/92 |
| 5,161,845 A | 11/1992 | Carpenter, Jr. | |
| 5,208,442 A * | 5/1993 | Ahola | H05H 1/38 219/121.48 |
| 5,255,285 A | 10/1993 | Aberl et al. | |
| 5,638,398 A | 6/1997 | Ikitsu et al. | |
| 5,757,841 A * | 5/1998 | Ikitsu | B23P 19/105 29/705 |
| 5,870,424 A | 2/1999 | Todoriki et al. | |
| 6,084,200 A * | 7/2000 | Ahola | B23K 10/00 219/121.36 |
| 6,167,076 A | 12/2000 | Ignacio | |
| 6,265,690 B1 * | 7/2001 | Fornsel | B05D 3/144 219/121.39 |
| 7,547,861 B2 * | 6/2009 | Jorgensen | H05H 1/34 164/46 |
| 7,660,337 B2 | 2/2010 | Teeples et al. | |
| 7,992,634 B2 | 8/2011 | Angelle et al. | |
| 9,383,278 B1 | 7/2016 | Schiller | |
| 2008/0084907 A1 | 4/2008 | Lehr et al. | |
| 2010/0272146 A1 | 10/2010 | Piccardi | |
| 2011/0089617 A1 | 4/2011 | Reali et al. | |
| 2011/0274137 A9 | 11/2011 | Piccardi | |
| 2015/0233195 A1 | 8/2015 | Smith et al. | |

FOREIGN PATENT DOCUMENTS

| | | | |
|---|---|---|---|
| IT | 1297835 A1 | | 8/1998 |
| JP | 3388329 | * | 3/2003 |

OTHER PUBLICATIONS

U.S. Appl. No. 14/693,862, filed Apr. 22, 2015, Schiller.
U.S. Appl. No. 14/796,964, filed Jul. 10, 2015, Schiller.
U.S. Appl. No. 15/146,877, filed May 4, 2016, Schiller.
U.S. Appl. No. 15/198,949, filed Jun. 30, 2016, Schiller.

* cited by examiner

ELECTRODE JOINING APPARATUS

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

This application is a non-provisional of U.S. Provisional Patent Application Ser. No. 61/982,337 filed Apr. 22, 2014 entitled Electrode Joining Apparatus and Methods of which is herein incorporated by reference in its entirety.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present invention relates generally to machinery for manipulating electrodes and more particularly to devices and methods for joining graphite electrodes for use with metal arc furnaces.

Metal arc furnaces include large vessels for melting metal. Heat may be generated inside the furnaces using graphite electrodes across which electric current is passed. Heat is generated inside the furnace due to a high voltage arc formed by the current passing through one or more electrodes. The heat is used to melt metal.

During use, graphite electrodes are consumed within the furnace vessel, requiring electrodes to be replaced over time. As electrode material is consumed in the furnace, the electrode is shortened to a length where it is no longer independently usable. However, a partially-consumed electrode may be joined to a second partially-consumed or complete electrode to form a joined electrode that can be used. Thus, the partially-consumed electrode may still be useful when placed in combination with a second electrode portion.

Electrodes may be joined in an end-to-end configuration using a threaded joint in some applications. When electrodes are combined, electrical conductivity is generally maintained across the joint, and electricity may be passed from one electrode to the second in the joint electrode. A threaded joint is commonly used to join electrodes. The joining procedure requires at least one electrode to be rotated relative to a second electrode such that a threaded engagement occurs.

Conventional tools and methods for joining electrodes having a threaded joint include powered electrode joining devices including an electrode holder that is configured to grip the fixed electrode having a threaded socket, and a torque device that is configured to grip and spin the free electrode with a threaded rod onto the fixed electrode, the threaded rod engaging the threaded socket to join the electrodes.

Often times the threaded socket in the fixed electrode can contain dust, debris, or graphite residue, particularly when the fixed electrode is a used electrode which has been removed from an active furnace. Dust, debris, or graphite residue contained in the threaded socket of the fixed electrode can negatively affect the quality of the joint formed between the fixed electrode and the free electrode. For instance, having stray particles in the threaded socket can negatively affect the electrical connectivity between the used electrode and the free electrode, which can adversely affect the efficiency of the metal arc furnace when the electrodes are subsequently used in the furnace.

What is needed then are improvements in electrode joining apparatuses that can help remove dust and debris from a fixed electrode positioned in the electrode joining apparatus.

BRIEF SUMMARY

One aspect of the disclosure provides an electrode joining apparatus for joining a free electrode to a fixed electrode, the fixed electrode having a top end. The apparatus can include an electrode holder configured to selectively hold the fixed electrode. A torque device can be positioned above the electrode holder, the torque device configured to grip and spin the free electrode to join the free electrode to the fixed electrode. A blowout jet can be oriented to selectively force a stream of gas toward the top end of the fixed electrode when the fixed electrode is held by the electrode holder. The fixed electrode can include a threaded socket in some embodiments, and the blowout jet can be oriented to selectively force the stream of gas toward the threaded socket.

In some embodiments, the electrode joining apparatus can include an axial passage defined in the electrode holder and the torque device, and the blowout jet can be oriented to selectively force a stream of air into the axial passage. The blowout jet can be connected to either the torque device, the electrode holder, or any other suitable structure on the electrode joining apparatus.

As such, the blowout jet can help remove dust, debris, or graphite residue on the top end of the fixed electrode before the free electrode is joined to the fixed electrode. The removal of dust and debris from the fixed electrode can help provide a cleaner joint between the fixed electrode and the free electrode, which can help increase the electrical connectivity between the fixed electrode and the free electrode, thereby helping increase the efficiency of the metal arc furnace utilizing the jointed electrodes.

One objective of the present disclosure is to help remove dust and debris from the top of a fixed electrode in an electrode joining apparatus before a free electrode is joined to the fixed electrode.

Another objective is to provide a stream of gas to the top end of a fixed electrode in an electrode joining apparatus before a free electrode is joined to the fixed electrode.

Another objective is to help increase the electrical connectivity across a joint formed between a fixed electrode and a free electrode in an electrode joining apparatus.

Numerous other objects, advantages and features of the present disclosure will be readily apparent to those of skill in the art upon a review of the following drawings and description of a preferred embodiment.

DETAILED DESCRIPTION

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention.

To facilitate the understanding of the embodiments described herein, a number of terms are defined below. The terms defined herein have meanings as commonly understood by a person of ordinary skill in the areas relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims.

As described herein, an upright position is considered to be the position of apparatus components while in proper operation or in a natural resting position as described herein. Vertical, horizontal, above, below, side, top, bottom and other orientation terms are described with respect to this upright position during operation unless otherwise specified. The term "when" is used to specify orientation for relative positions of components, not as a temporal limitation of the claims or apparatus described and claimed herein unless otherwise specified.

The phrase "in one embodiment," as used herein does not necessarily refer to the same embodiment, although it may. Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the apparatuses and/or methods disclosed and claimed herein may be made and/or executed without undue experimentation in light of the present disclosure. While the apparatuses and methods of this invention have been described in terms of the embodiments included herein, it will be apparent to those of ordinary skill in the art that variations may be applied to the apparatuses and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Figure 1:
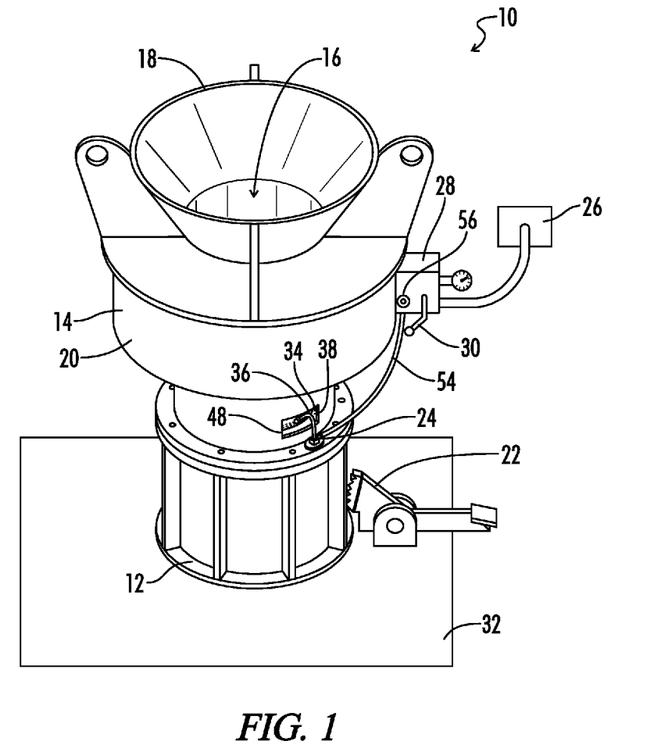
FIG. 1 is a perspective view of an embodiment of an electrode joining apparatus including a blowout jet.

Referring now to the drawings, an embodiment of an electrode joining apparatus 10 is shown in FIG. 1. Electrode joining apparatus 10 can include electrode holder 12 and torque device 14. An axial passage 16 can extend through electrode holder 12 and torque device 14, axial passage 16 allowing passage of one or more electrodes through electrode joining apparatus 10. In some embodiments, torque device 14 can include an upper funnel 18 which can facilitate centering of an electrode being lowered into electrode joining apparatus 10 through axial passage 16.

In some applications, graphite electrodes can be joined in an end to end fashion using a threaded joint. Joining the electrodes requires one electrode to be rotated relative to the other electrode. In such applications, a fixed electrode 34 can be selectively received and held by electrode holder 12 and torque device 14 can be configured to grip and spin a free electrode down onto fixed electrode 34 to effectively join the two electrodes together. Fixed electrode 34 can include a threaded socket 36, and a free electrode can include a threaded rod, the threaded rod engaging threaded socket 36 to join the two electrodes together. Electrode holder 12 can include a holder grip 22 which can be rotated to selectively fix or clamp fixed electrode 34 within electrode holder 12. In some embodiments, electrode holder 12 can be configured to prevent rotational or axial movement of fixed electrode 34 once the holder grip 22 engages fixed electrode 34. Electrode holder 12 can be securely fixed to a platform 32 on which operators can work.

In some embodiments, torque device 14 can include machinery which can rotate a free electrode lowered through funnel 18 into torque device 14. The machinery can be contained in housing 20. The machinery can generally grip the lower end of the free electrode and apply a rotational force to the free electrode. In some embodiments, the machinery can be powered by a mechanical actuator 26 such as a hydraulic pressure system, or a pneumatic pressure system. In other embodiments, torque device 14 can be powered electrically or manually. In some embodiments, torque device 14 can include control console 28. Control console 28 can include lever 30 which can be used to control the supply of input such as hydraulic or pneumatic pressure or mechanical force to torque device 14.

In other embodiments, control console 28 can be placed in a separate location such as a control room or other remote location and torque device 14 can be operated without an operator being present near electrode joining apparatus 10. In some embodiments, control console 28 can be electrically connected to torque device 14, while in other embodiments control console 28 can communicate with torque device 14 through wireless telemetry.

Figure 2:
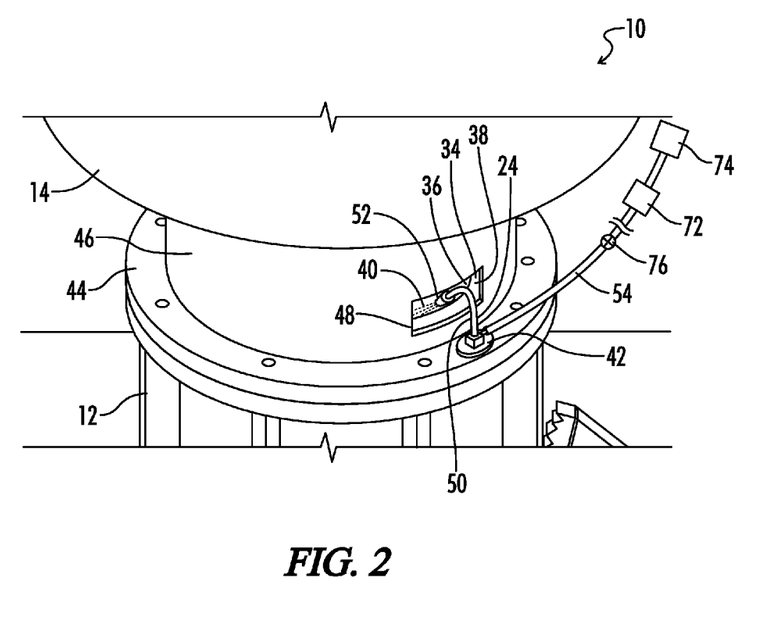
FIG. 2 is a detailed view of the blowout jet of FIG. 1.
Figure 3:
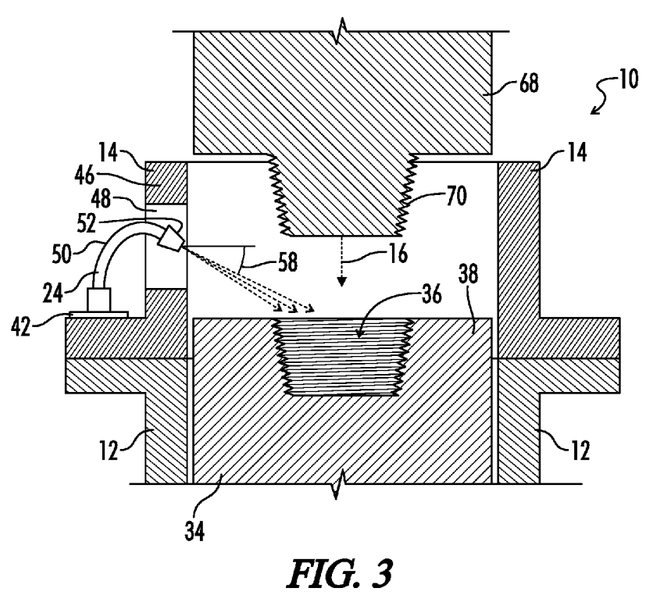
FIG. 3 is a partial cross section view of the electrode joining apparatus of FIG. 1 showing a fixed electrode disposed in the electrode joining apparatus.

Often times fixed electrode 34 which is lowered into electrode joining apparatus 10 can contain dust, debris, or graphite residue in threaded socket 36 located in a top end 38 of fixed electrode 34. To help combat this problem, electrode joining apparatus 10 can include a blowout jet 24 oriented to force a stream of gas 40 into the axial passage 16 towards the top end 38 of fixed electrode 34 when fixed electrode 34 is held by electrode holder 12, as shown in FIGS. 2 and 3. In some embodiments, blowout jet 24 can be oriented to force a stream of gas 40 toward threaded socket 36. Blowout jet 24 can force a stream of gas into axial passage 16 at a downward angle 58 with respect to a horizontal plane, as shown in FIG. 3. As such, blowout jet 24 can blow gas down and into threaded socket 36 in fixed electrode 34.

In some embodiments, electrode joining apparatus 10 can be an off-furnace type electrode joining apparatus 10, with fixed electrode 34 being removed from a furnace and placed in electrode joining apparatus 10 which is separated from the furnace. In other embodiments, electrode joining apparatus 10 can be an on-furnace type electrode joining apparatus 10, where a free electrode is joined to a fixed electrode 34 while fixed electrode 34 is still disposed in the furnace.

As such, stream of gas 40 can help remove dust and debris contained in threaded socket 36 to help produce a cleaner joint between fixed electrode 34 and a free electrode joined to fixed electrode 34. Removing the dust and debris from threaded socket 36 can help increase the electrical connectivity between fixed electrode 34 and a free electrode, which can help increase the efficiency of the metal arc furnace when the joined electrodes are returned to the furnace.

In FIGS. 2 and 3, blowout jet 24 is mounted to torque device 14 via connection plate 42. Torque device 14 can include a lower flange 44 and torque riser section 46, torque riser section 46 extended upward to machinery housing 20. In some embodiments, blowout jet 24 can be mounted to lower flange 44 on torque device 14. In some embodiments, torque device 14 can include torque device viewing window 48, and blowout jet 24 can be oriented to force stream of gas 40 through torque device viewing window 48 into axial passage 16 toward top end 38 of fixed electrode 34. In some embodiments, torque device viewing window 48 can be located in torque device riser section 46.

Many conventional electrode joining apparatuses include a torque device 14 having a lower flange 44 and a torque device viewing window 48 located in a torque device riser section 46. Torque device viewing window 48 can generally be used to view the position of fixed electrode 34 or a free electrode within electrode joining apparatus 10. As such, a conventional electrode joining apparatus can be retrofitted with a blowout jet 24 by mounting the blowout jet 24 to lower flange 44 of torque device 14, and orienting blowout jet 24 to selectively force a stream of gas 40 through torque device viewing window 48 in torque device riser section 46 such that stream of gas 40 is oriented towards top end 38 of fixed electrode 34.

In some embodiments, blowout jet 24 can include a hose 50 coupled to a nozzle 52. Nozzle 52 can be configured to produce a stream of gas when a compressed gas is supplied to the blowout jet 24. The shape of nozzle 52 can be tailored to produce different flow profiles. Hose 50 can be a flexible hose in some embodiments. In other embodiments, hose 50 can be substantially rigid. Hose 50 can be made from a variety of suitable materials, including but not limited to nylon, polyurethane, polyethylene, PVC, natural rubbers, or synthetic rubbers.

Referring again to FIG. 1, in some embodiments torque device 14 can be driven by a pneumatic input 26. In such embodiments, gas can be supplied to blowout jet 24 from pneumatic input 26 by a compressed gas line 54 communicated between pneumatic input 26 and blowout jet 24. In some embodiments, torque device 14 can include control console 28, and compressed gas line 54 can be communicated with pneumatic input 26 via control console 28. Control console 28 can be configured to selectively supply compressed gas from pneumatic input 26 to blowout jet 24 via compressed gas line 54. In some embodiments, control console 28 can include a push button 56 or lever which when actuated can send compressed gas to blowout jet 24. As such, an operator can control both torque device 14 and blowout jet 24 from control console 28. In some embodiments, control console 28 can be located in a control room or other distant location such that torque device 14 and blowout jet 24 can be controlled by an operator without the operator having to be present near electrode joining apparatus 10, which can be potentially dangerous.

In other embodiments, torque device 14 is driven by another type of input, such as a hydraulic or an electric input. In such embodiments, as shown in FIG. 2, electrode joining apparatus 10 can include a separate pneumatic supply such as a compressed gas tank 72 coupled to a compressor 74. A valve 76 can selectively communicate compressed gas tank 72 with blowout jet 24, valve 76 being selectively opened to supply a compressed gas to blowout jet 24 from compressed gas tank 72 such that blowout jet 24 can selectively force a stream of gas 40 toward top end 38 of fixed electrode 34. In some embodiments valve 76 can be a solenoid valve which can be electrically actuated by an independent control mechanism or by a control console for torque device 14. Control console can be mounted to torque device 14 or control console can be physically separated from torque device 14, control console operating torque device 14 and valve 76 remotely or using wireless telemetry. In still other embodiments, compressed gas can be supplied to blowout jet 24 by a facility pneumatic line, blowout jet 24 configured to couple to the facility pneumatic line.

Figure 4:
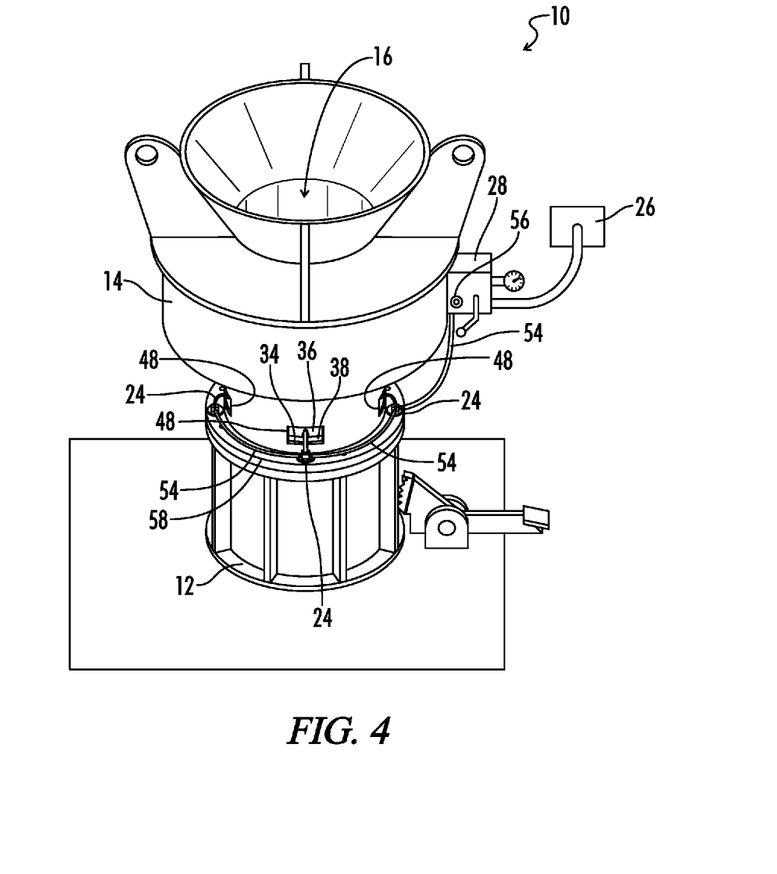
FIG. 4 is a perspective view of another embodiment of an electrode joining apparatus including multiple blowout jets.
Figure 5:
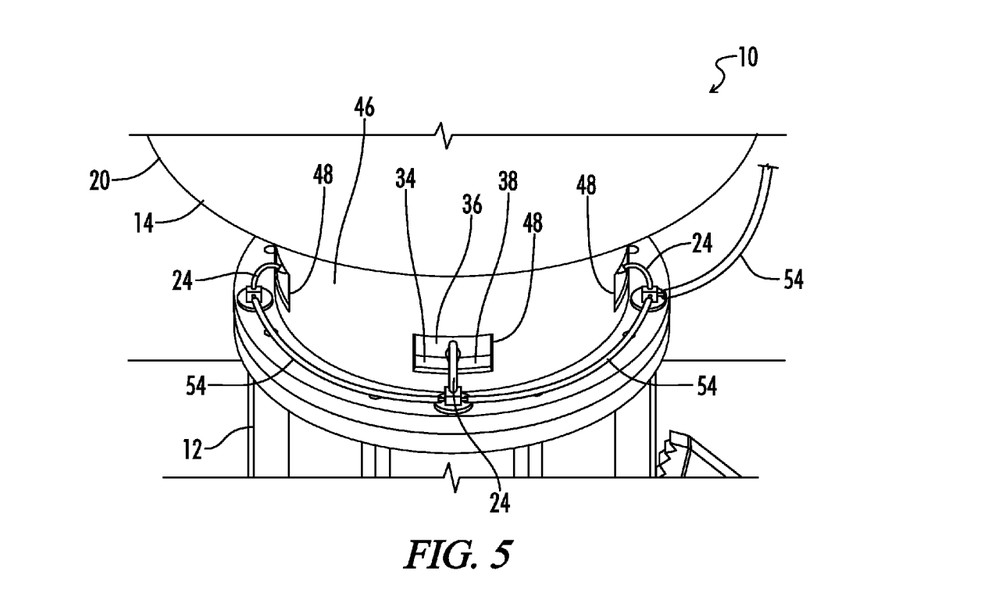
FIG. 5 is a detailed view of the multiple blowout jets of FIG. 4.
Figure 6:
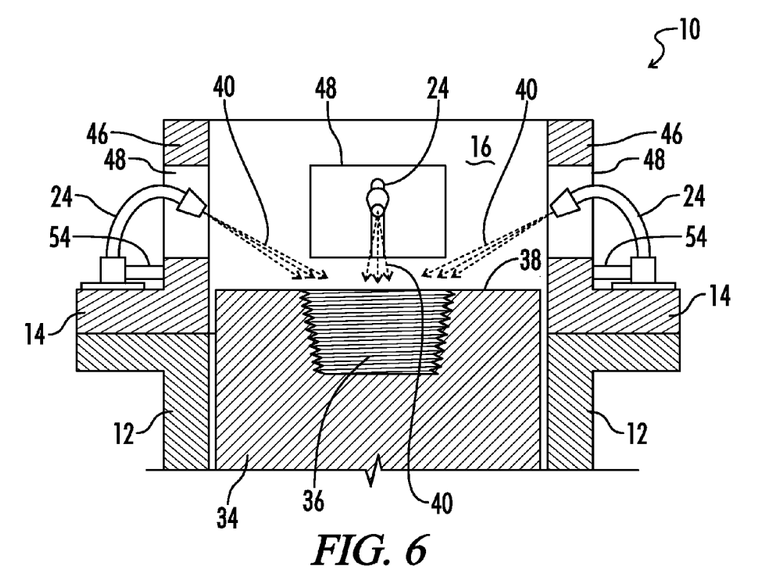
FIG. 6 is a partial cross section view of the electrode joining apparatus of FIG. 4 showing a fixed electrode disposed in the electrode joining apparatus.

Another embodiment of an electrode joining apparatus 10 is shown in FIGS. 4-6. Electrode joining apparatus 10 can include multiple blowout jets 24. Each blowout jet 24 can be oriented to force a separate stream of gas 40 toward the top end 38 of fixed electrode 34 when fixed electrode 34 is held by electrode holder 12. In FIGS. 4-6, each of blowout jets 24 is mounted to torque device 14. Each of blowout jets 24 is also oriented to force a stream of gas 40 through a corresponding torque device viewing window 48.

In some embodiments, multiple blowout jets 24 can be mounted generally on one side of electrode joining apparatus 10. For instance in some embodiments, torque device 14 can include a perimeter 58, and multiple blowout jets 24 can be positioned around only a portion of perimeter 58. As such, multiple blowout jets 24 generally only force streams of gas 40 toward top end 38 of fixed electrode 34 from one side of electronic joining apparatus 10 and one side of fixed electrode 34. In doing so, streams of gas 40 can generally urge dust and debris in threaded socket 36 towards one side of fixed electrode 34 such that streams of gas 40 can urge dust and debris out of threaded socket 36, as opposed to blowout jets 24 and streams of gas 40 working against one another.

In some embodiments, as shown in FIGS. 4-6, multiple blowout jets 24 can be pneumatically coupled in series, such that when push button 56 on control console 28 is actuated, compressed gas from pneumatic input 26 can be fed to each of blowout jets 24. Multiple blowout jets 24 can be pneumatically coupled by multiple compressed gas lines 54. In other embodiments, multiple blowout jets 24 can be connected in parallel, with an independent compressed gas line running from control console 28, pneumatic input 26 to each of blowout jets 24. In still other embodiments, the input for torque device 14 can be a hydraulic or electric input, and electrode joining apparatus 10 can include a separate pneumatic supply such as the compressed gas tank 72 and compressor 76 shown in FIG. 2, and blowout jets 24 can be either coupled in series or in parallel with compressed gas tank 72 and valve 76 such that when valve 76 is actuated compressed gas is supply to each of multiple blowout jets 24.

Figure 7:
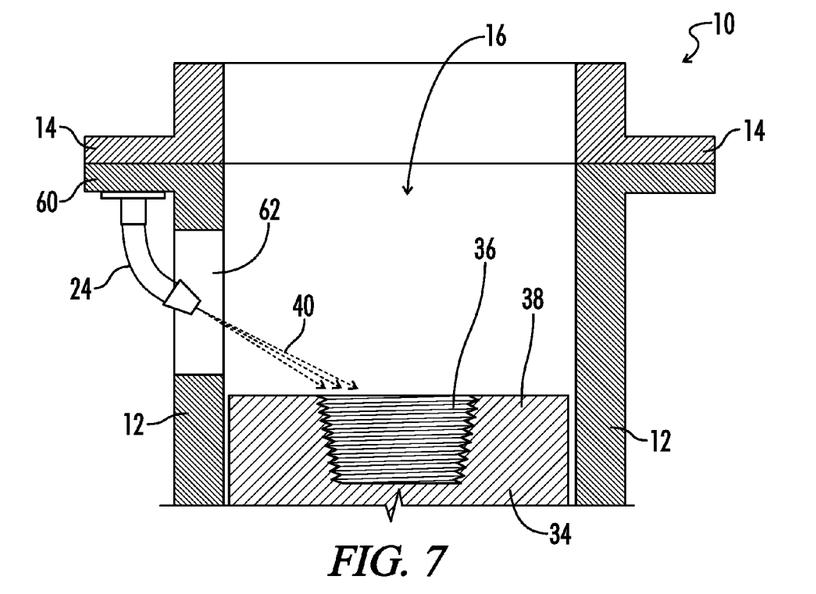
FIG. 7 is a partial cross section view of another embodiment of an electronic joining apparatus having a blowout jet mounted to an electrode holder.

While blowout jets 24 are shown in FIGS. 1-6 mounted to torque device 14, blowout jets 24 can be connected to any suitable structure on electrode joining apparatus 10. For instance, an embodiment of electrode joining apparatus 10 is shown in FIG. 7 with blowout jet 24 mounted to electrode holder 12. Electrode holder 12 can include top flange 60, and blowout jet 24 can be mounted to top flange 60, blowout jet 24 extending downward from top flange 60. Electrode holder 12 can include an electrode holder viewing window 62, and blowout jet 24 can be oriented to force a stream of gas 40 through electrode holder viewing window 62 and toward top end 38 of fixed electrode 34.

Figure 8:
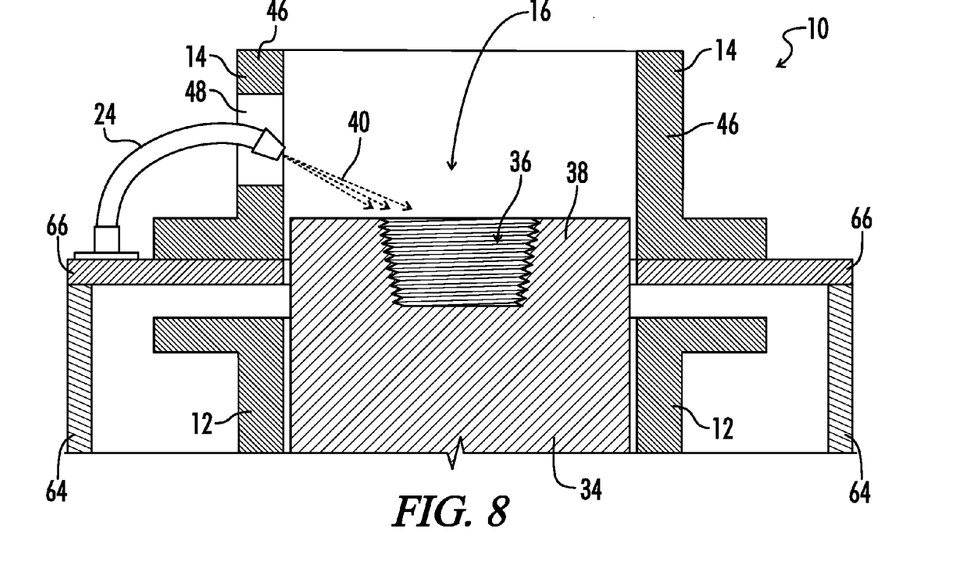
FIG. 8 is a partial cross section view of another embodiment of an electrode joining apparatus including a torque device lift with a carriage for a torque device, and a blowout jet mounted on the top of the carriage.
Figure 9:
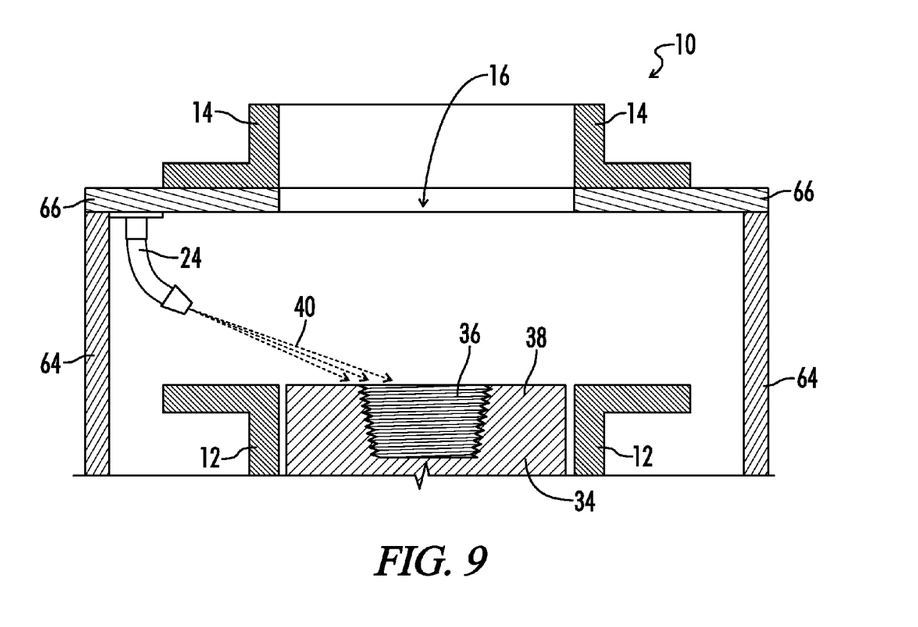
FIG. 9 is a partial cross section view of another embodiment of an electrode joining apparatus including a torque device lift with a carriage for a torque device, and a blowout jet mounted on the bottom of the carriage.

Other embodiments of an electrode joining apparatus 10 including a torque device lift 64 is shown in FIGS. 8-9. Torque device lift 64 can be configured to vary the vertical position of torque device 14. In some electrode joining procedures, when a used or fixed electrode 34 is lowered into electrode joining apparatus 10, the dimensions of an electrode carrier on a crane may limit the distance fixed electrode 34 can be lowered into electrode joining apparatus 10 such that the top of the fixed electrode 34 is above torque device 14. It may then be necessary to raise torque device 14 such that torque device 14 can engage a free electrode positioned above the used or fixed electrode 34.

Torque device lift 64 can include carriage 66 on which torque device 14 can be positioned. Torque device lift 64 can then move carriage 66 and effectively torque device 14 vertically to vary the position of torque device 14 as necessary. Lift 64 can include any suitable mechanism for lifting torque device 14 via carriage 66, including a hydraulic, pneumatic, or electric lift mechanism. In embodiments including a torque device lift 64, blowout jet 24 can also be mounted to carriage 66 of lift 64. In some embodiments, as shown in FIG. 8, blowout jet 24 can be mounted to the top of carriage 66 of torque device lift 64, and blowout jet 24 can extend through torque device viewing window 48 to force a stream of gas into axial passage 16. In other embodiments, as shown in FIG. 9, blowout jet 24 can be mounted to the bottom of carriage 66 on torque device lift 64.

Another aspect of the present disclosure is a method, exemplified in FIG. 3, for joining a fixed electrode 34 and a free electrode 68 with an electrode joining apparatus 10 including an electrode holder 12 configured to selectively hold fixed electrode 34, a torque device 14 configured to grip and spin free electrode 68 onto fixed electrode 34, an axial passage 16 defined through electrode holder 12 and torque device 14, and a blowout jet 24 oriented to force a stream of gas 40 into axial passage 16. The method includes the steps of lowering a fixed electrode 34 into electrode joining apparatus 10 and clamping fixed electrode 34 with electrode holder 12 such that blowout jet 24 is oriented towards a top end 38 of fixed electrode 34; forcing a stream of gas 40 from blowout jet 24 into axial passage 16 towards top end 38 of fixed electrode 34; lowering a free electrode 68 into torque device 14; and spinning free electrode 68 with torque device 14 to join fixed electrode 34 and free electrode 68 together. As such, a threaded socket 36 of fixed electrode 34 can be blown out before being joined to a threaded rod 70 of free electrode 68.

Thus, although there have been described particular embodiments of the present invention of a new and useful Electrode Blowout Jet, it is not intended that such references be construed as limitations upon the scope of this invention.

What is claimed is:

1. An electrode joining apparatus for joining a free electrode to a fixed electrode, the fixed electrode having a top end, the apparatus comprising:
   an electrode holder configured to selectively hold the fixed electrode;
   a torque device positioned above the electrode holder, the torque device configured to grip and spin the free electrode to join the free electrode to the fixed electrode; and
   multiple blowout jets, each blowout jet oriented to force a stream of gas towards the top end of the fixed electrode when the fixed electrode is held by the electrode holder.

2. The apparatus of claim 1, wherein the multiple blowout jets are pneumatically coupled in series by multiple compressed gas lines.

3. The apparatus of claim 1, wherein the multiple blowout jets are positioned around a portion of the perimeter of the torque device.

4. An electrode joining apparatus for joining a free electrode to a fixed electrode, the fixed electrode having a top end, the apparatus comprising:
   an electrode holder configured to selectively hold the fixed electrode;
   a torque device positioned above the electrode holder, the torque device configured to grip and spin the free electrode to join the free electrode to the fixed electrode; and
   a blowout jet oriented to selectively force a stream of gas toward the top end of the fixed electrode when the fixed electrode is held by the electrode holder, wherein the blowout jet is mounted to the torque device,
   wherein the torque device includes a torque device viewing window, and the blowout jet is oriented to selectively force the stream of gas through the torque device viewing window toward the top end of the fixed electrode when the fixed electrode is held by the electrode holder.

5. The apparatus of claim 4, wherein the torque device includes a torque device riser section, and the torque device viewing window is defined in the torque device riser section.

6. An electrode joining apparatus for joining a free electrode to a fixed electrode, the fixed electrode having a top end, the apparatus comprising:
   an electrode holder configured to selectively hold the fixed electrode;
   a torque device positioned above the electrode holder, the torque device configured to grip and spin the free electrode to join the free electrode to the fixed electrode; and
   a blowout jet oriented to selectively force a stream of gas toward the top end of the fixed electrode when the fixed electrode is held by the electrode holder, wherein the blowout jet is mounted to the electrode holder,
   wherein the electrode holder includes an electrode holder viewing window, and the blowout jet is oriented to selectively force the stream of gas through the electrode holder viewing window toward the top end of the fixed electrode when the fixed electrode is held by the electrode holder.

7. The apparatus of claim 6, wherein the torque device includes a pneumatic input, and gas is supplied to the blowout jet by a compressed gas line communicated with the pneumatic input.

8. The apparatus of claim 7, wherein the torque device comprises a control console, and the compressed gas line is communicated with the pneumatic input via the control console, the control console configured to selectively supply compressed gas from the pneumatic input to the blowout jet.

* * * * *